United States Patent
Swalwell

(10) Patent No.: US 8,928,881 B2
(45) Date of Patent: Jan. 6, 2015

(54) CYTOMETER WITH AUTOMATIC CONTINUOUS ALIGNMENT CORRECTION

(75) Inventor: Jarred E. Swalwell, Shoreline, WA (US)

(73) Assignee: University of Washington, Seattle, WA (US)

( * ) Notice: Subject to any disclaimer, the term of this patent is extended or adjusted under 35 U.S.C. 154(b) by 705 days.

(21) Appl. No.: 13/144,689

(22) PCT Filed: Jan. 22, 2010

(86) PCT No.: PCT/US2010/021817
§ 371 (c)(1),
(2), (4) Date: Jul. 14, 2011

(87) PCT Pub. No.: WO2010/085655
PCT Pub. Date: Jul. 29, 2010

(65) Prior Publication Data
US 2011/0267604 A1    Nov. 3, 2011

Related U.S. Application Data

(60) Provisional application No. 61/147,035, filed on Jan. 23, 2009, provisional application No. 61/147,060, filed on Jan. 23, 2009.

(51) Int. Cl.
*G01N 15/14* (2006.01)
*G01N 21/49* (2006.01)

(52) U.S. Cl.
CPC ........ *G01N 15/1425* (2013.01); *G01N 15/1434* (2013.01); *G01N 21/49* (2013.01); *G01N 15/1429* (2013.01); *G01N 15/1459* (2013.01); *G01N 2015/1402* (2013.01); *G01N 2015/1452* (2013.01)

USPC ............................................ 356/338; 356/336

(58) Field of Classification Search
CPC ...................... G01N 15/1425; G01N 15/1434
USPC ............... 356/28, 28.5, 139.04, 139.08, 150; 702/94; 422/108
See application file for complete search history.

(56) References Cited

U.S. PATENT DOCUMENTS 3,241,430 A * 3/1966 Kulick ........................... 356/150
3,316,799 A * 5/1967 Daley et al. ................ 356/152.2

(Continued)

FOREIGN PATENT DOCUMENTS

| EP | 0 200 851 A2 | 11/1986 |
| WO | 00/11024 A2 | 3/2000 |
| WO | 2004/104178 A2 | 12/2004 |

OTHER PUBLICATIONS

International Search Report and Written Opinion mailed Oct. 8, 2010, issued in corresponding International Application No. No. PCT/US2010/021817, filed Jan. 22, 2010, 7 pages.

*Primary Examiner* — Ari M Diacou
(74) *Attorney, Agent, or Firm* — Christensen O'Connor Johnson Kindness PLLC

(57) ABSTRACT

A system and method for performing flow cytometry is disclosed wherein the alignment of the light source with respect to the sensing region of the fluid stream is continuously controlled using a feedback control loop. An imaging apparatus is provided that images the system along the optical axis, between the field stop and the sensing region. In an embodiment, the cytometer includes a field stop having an H-shaped aperture and light diverters over the ends of the aperture that divert a portion of the light to peripheral detectors.

23 Claims, 5 Drawing Sheets

(56) References Cited

U.S. PATENT DOCUMENTS

| | | | |
|---|---|---|---|
| 3,320,424 A * | 5/1967 | Olson et al. ................ 250/230 |
| 3,542,478 A * | 11/1970 | Dessus ........................ 356/153 |
| 3,669,549 A * | 6/1972 | Besson et al. ............. 356/141.4 |
| 3,738,754 A * | 6/1973 | Marcy et al. ................ 356/498 |
| 3,972,620 A * | 8/1976 | Nauth .......................... 356/150 |
| 4,054,388 A * | 10/1977 | Marsh et al. ................ 356/400 |
| 4,154,530 A * | 5/1979 | Connolly et al. ........ 356/139.05 |
| 4,189,234 A * | 2/1980 | Bryant ....................... 356/141.3 |
| 4,251,160 A * | 2/1981 | Bouwhuis et al. ........... 356/401 |
| 4,291,976 A * | 9/1981 | McMahon ..................... 341/14 |
| 4,311,385 A * | 1/1982 | Keene ...................... 356/139.08 |
| 4,314,762 A * | 2/1982 | Gresko ........................ 356/150 |
| 4,320,462 A * | 3/1982 | Lund et al. .................. 356/121 |
| 4,492,859 A * | 1/1985 | Pruszenski, Jr. ............. 250/216 |
| 4,576,480 A * | 3/1986 | Travis ....................... 356/139.05 |
| 4,644,172 A * | 2/1987 | Sandland et al. ............ 250/548 |
| 4,690,561 A * | 9/1987 | Ito ................................ 356/339 |
| 4,732,479 A * | 3/1988 | Tanaka et al. ............... 356/336 |
| 4,741,043 A * | 4/1988 | Bacus ........................... 382/129 |
| 5,007,737 A * | 4/1991 | Hirleman, Jr. ................ 356/336 |
| 5,144,479 A * | 9/1992 | Aharon et al. ............... 359/424 |
| 5,179,418 A * | 1/1993 | Takamiya et al. .......... 356/28.5 |
| 5,412,200 A * | 5/1995 | Rhoads ...................... 250/201.9 |
| 5,461,472 A * | 10/1995 | Harvey et al. ............... 356/138 |
| 5,473,706 A * | 12/1995 | Bacus et al. ................. 382/133 |
| 5,576,827 A * | 11/1996 | Strickland et al. ........... 356/336 |
| 5,689,110 A * | 11/1997 | Dietz et al. ................ 250/252.1 |
| 5,719,667 A * | 2/1998 | Miers ............................ 356/73 |
| 5,844,685 A * | 12/1998 | Gontin ......................... 356/433 |
| 5,872,627 A * | 2/1999 | Miers .......................... 356/338 |
| 5,936,253 A * | 8/1999 | Sugaya ....................... 250/548 |
| 5,936,729 A * | 8/1999 | Igushi ......................... 356/336 |
| 6,021,975 A * | 2/2000 | Livingston ................. 244/3.11 |
| 6,061,131 A * | 5/2000 | Igushi et al. ................ 356/336 |
| 6,069,690 A * | 5/2000 | Xu et al. ....................... 356/73 |
| 6,079,836 A * | 6/2000 | Burr et al. ..................... 356/70 |
| 6,256,088 B1 * | 7/2001 | Gordon .......................... 356/73 |
| 6,288,780 B1 * | 9/2001 | Fairley et al. ............. 356/237.1 |
| 6,301,007 B1 * | 10/2001 | Hanlon et al. ................ 356/400 |
| 6,327,031 B1 * | 12/2001 | Gordon .......................... 356/72 |
| 6,400,454 B1 * | 6/2002 | Noguchi et al. ........... 356/237.3 |
| 6,473,171 B1 * | 10/2002 | Buttry et al. ................. 356/246 |
| 6,654,112 B2 * | 11/2003 | Noguchi et al. ........... 356/237.3 |
| 6,792,369 B2 * | 9/2004 | Messina ........................ 702/94 |
| 6,875,973 B2 * | 4/2005 | Ortyn et al. ................ 250/201.3 |
| 6,947,577 B2 * | 9/2005 | Stam et al. ................... 382/104 |
| 7,006,234 B1 * | 2/2006 | Cottrell et al. ............... 356/515 |
| 7,362,424 B2 * | 4/2008 | van den Engh et al. ........ 356/73 |
| 7,788,067 B2 * | 8/2010 | Bachalo et al. .............. 702/193 |
| 7,920,261 B2 * | 4/2011 | Jeys et al. .................... 356/338 |
| 8,184,271 B2 * | 5/2012 | Pittaro et al. .................. 356/28 |
| 8,531,657 B2 * | 9/2013 | Fasse et al. ............. 356/139.04 |
| 2002/0041376 A1 * | 4/2002 | Kurozumi et al. ........... 356/338 |
| 2002/0145726 A1 * | 10/2002 | Chao et al. ..................... 356/28 |
| 2003/0044967 A1 * | 3/2003 | Heffelfinger et al. ...... 435/287.2 |
| 2003/0202175 A1 * | 10/2003 | van den Engh et al. ...... 356/138 |
| 2003/0210391 A1 * | 11/2003 | Uto et al. .................. 356/237.1 |
| 2004/0030519 A1 * | 2/2004 | Messina ........................ 702/94 |
| 2004/0070757 A1 * | 4/2004 | Moore et al. ................. 356/339 |
| 2004/0169867 A1 * | 9/2004 | Sharpe .......................... 356/621 |
| 2004/0217256 A1 * | 11/2004 | Ortyn et al. ................ 250/201.4 |
| 2005/0030534 A1 | 2/2005 | Oldham |
| 2005/0062962 A1 * | 3/2005 | Fairley et al. ............. 356/237.2 |
| 2005/0157310 A1 * | 7/2005 | Kim et al. .................... 356/510 |
| 2006/0033931 A1 * | 2/2006 | Lau et al. ..................... 356/493 |
| 2006/0134002 A1 | 6/2006 | Lin |

* cited by examiner

CYTOMETER WITH AUTOMATIC CONTINUOUS ALIGNMENT CORRECTION

CROSS-REFERENCES TO RELATED APPLICATIONS

This application claims the benefit of U.S. Provisional Application No. 61/147,060, filed Jan. 23, 2009, and further claims the benefit of U.S. Provisional Application No. 61/147,035, filed Jan. 23, 2009, the disclosures of which are hereby expressly incorporated by reference in their entirety.

STATEMENT OF GOVERNMENT LICENSE RIGHTS

This invention was made with Government support under Contract No. OCE 622247 awarded by the National Science Foundation. The Government has certain rights in the invention.

BACKGROUND

Flow cytometry is a well-known technique for counting and/or otherwise examining microscopic particles, such as cells and the like, by passing a stream of fluid in which the particles are suspended through a detection apparatus. The detection apparatus typically relies on detecting the optical response produced as the particles pass through an illuminated region of the device. In prior art microbial flow cytometers, for example, individual particles pass through an illumination zone, typically at a rate on the order of 1,000 cells per second, and detectors, gated electronically, measure the magnitude of a pulse representing the light scattered by the cells. The pulse magnitudes (or other properties) may then be processed to characterize the cells by a particular parameter of interest. For example, the angular dependence of scattered light may provide information on the nature of the scattering particles. More importantly, the fluorescent properties of the particles (which may be caused by appropriate fluorophores being added to the suspension) may provide desired parametric information.

Traditional flow cytometers use a clear sheath fluid to position particles or cells for cytometric measurements. An exemplary flow cytometry system is disclosed, for example, in U.S. Pat. No. 5,760,900, which is hereby incorporated by reference herein in its entirety. A new sheathless flow technology for cytometry systems is disclosed in the inventor's co-pending U.S. patent application Ser. No. 12/027,961 (U.S. Patent Publication No. 2008/0186479), which is hereby incorporated by reference in its entirety.

Flow cytometry has several advantages, including the ability to obtain multi-parametric data and high-speed data acquisition.

The alignment (or tuning) of a flow cytometer typically involves manually aligning the sheath stream (or cuvette) with the optical path of the system and adjusting the position of the light source (e.g., laser) with respect to the measurement or sensing region. The alignment of the flow cytometer can drift due to a number of factors; for example, thermal changes affecting the mechanical components of the system, pointing instability of the laser, and/or external interference, such as mechanical vibrations or the like. After the initial system alignment, the operator is typically tasked with maintaining the alignment, oftentimes making small adjustments to the laser position between each sample. Therefore, the time spent keeping a flow cytometer aligned throughout the day can be significant and the quality of the data between such alignments may be less than optimal.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A cytometry system is disclosed wherein a fluid stream with a plurality of particles suspended therein is illuminated at a sensing region with a light source, such as one or more lasers. An objective receives light from the sensing region that is focused along an optical axis towards a field stop aperture. A beam splitter is positioned between the lens and the field stop, intersecting the optical axis at an angle, and an imaging device; for example, a CCD camera is positioned toward the beam splitter and oriented to generate a picture along the optical axis. An XY stage defining a support surface that is precisely controllable in at least two orthogonal directions supports an optical element that controls the alignment of the light source with respect to the sensing region in the fluid stream. A computing device receives the images generated by the imaging device and calculates from the images at least one parameter that characterizes the alignment of the light source with the sensing region, wherein at least one calculated parameter is used to generate control signals that are transmitted to the XY stage such that a desired alignment of the light source with the sensing region is maintained.

In an embodiment of the invention, the generated images comprise digital images defined by a two-dimensional array of pixels, each pixel having an intensity; and further, the first parameter comprises a first array of the row sum of the image pixel intensities and the second parameter comprises a second array of the column sum of the image pixel intensities.

In an embodiment of the invention, the field stop aperture is H-shaped, having relatively large end portions and a relatively small center portion, the system further comprising first and second light deflectors disposed over the relatively large end portions, and associated first and second light detectors that receive light deflected by the first and second light deflectors, respectively.

A method for performing flow cytometry of a fluid stream having a plurality of particles suspended therein with a cytometer is disclosed, which includes directing a light source focused on a sensing region of the fluid stream and providing an optical system that receives light from the sensing region of the fluid stream and focuses the light along an optical axis that intersects a field stop having an aperture. A beam splitter is provided between the optical system and the field stop that is positioned to intersect the optical axis at an angle. With the cytometer operating, the cytometer is aligned and image data along the optical axis is taken from the beam splitter, and then analyzed and parameterized for the aligned system. An XY stage defining a support surface that is precisely controllable in at least two orthogonal directions, wherein the XY stage supports an optical element that determines the alignment of the light source focus with respect to the sensing region, is provided, calculating from the image along the optical axis a parameter that characterizes the alignment of the light source with the sensing region for the aligned system. During continuous operation of the cytometer, the beam splitter is used to obtain image data along the optical axis that is parameterized and compared with the aligned data to characterize the alignment of the light source with the sensing region. The data is used to generate and send control signals to the XY stage such that the optical element that determines the alignment of the light source is maintained in an aligned position.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A method and an apparatus are disclosed for continuous automated alignment of a flow cytometry system. In a preferred embodiment, the alignment system obtains and uses a video image of a portion of the flow cytometer, and analyzes the obtained images to automatically compensate for misalignment, which may result from thermal drift, laser pointing instability, external influences, and the like. In a current embodiment, the method includes aligning the cytometer and obtaining a video image of a portion of the aligned cytometer during operation, generally in a plane perpendicular to the optical axis between the fluid stream sensing region and the field stop. If necessary, the video image is digitized in whole or in part. The image pixel information is summed (or averaged) along two orthogonal directions, referred to herein as "rows" and "columns," to produce arrays representing the column and row sums for the aligned system. The process may be repeated for multiple images, averaging the results to reduce noise. During operation of the cytometer, video images of the same portion of the cytometer are continuously or intermittently obtained, and the corresponding image pixel information is averaged or summed in the same row/column orthogonal directions. The column and row averages or sums during operation are compared with the corresponding values obtained for the aligned system, and the comparison is used in a feedback system to control an XY stage (also referred to as an X-Y table) that controls the position of the light source beam relative to the sensing region.

Figure 1:
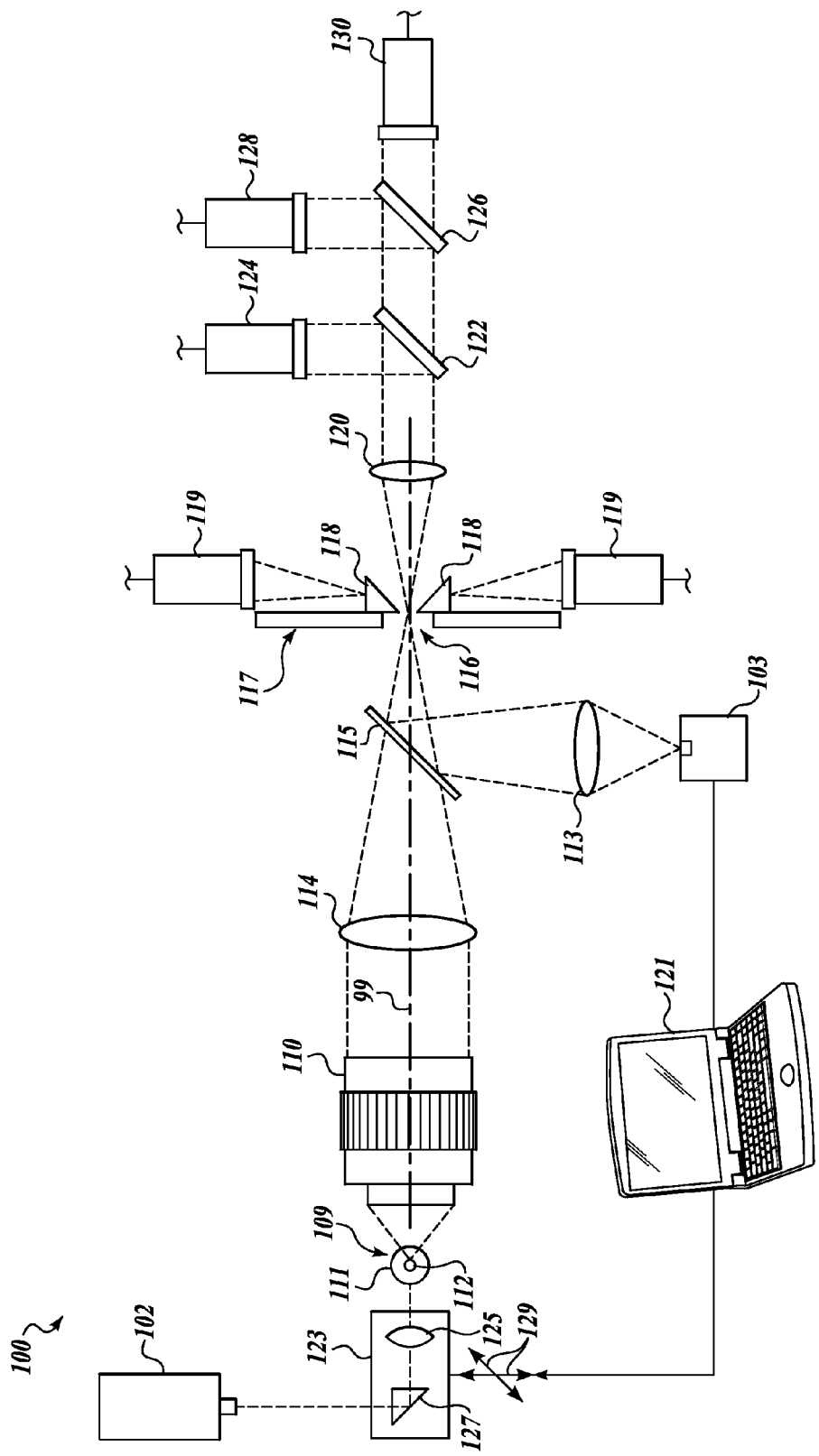
FIG. 1 shows schematically a cytometry system in accordance with the present invention.

An exemplary flow cytometry system 100 incorporating an auto-alignment component in accordance with the present invention is shown in FIG. 1. In this figure, which may be interpreted as a plan view of the cytometry system 100, a fluid stream 109 containing particles 112 of interest (for example, cells) flows through a sensing region 111 (in FIG. 1 the direction of flow is perpendicular to the figure). One or more light sources 102, typically but not necessarily lasers, project light through the sensing region 111. The projected light interacts with the particles 112 as they pass through the sensing region 111, for example, scattering the light and/or inducing at least some of the particles to fluoresce. A portion of the light exiting the sensing region 111 is received by an objective 110 and focused by a lens 114 through an optical aperture 116 in a field stop 117. The objective 110 and lens 114 define the optical axis 99 for the system 100.

Although not required for the present invention, in the system 100 the optical aperture 116 is H-shaped, wherein prisms overlie the larger end portions of the H-shaped aperture. The light deflectors 118 direct at least a portion of the incident light towards peripheral light detectors 119, for example, photomultiplier tubes (PMTs). Light passing through the smaller center portion of the optical aperture 116 encounters a lens 120 and is directed towards a first light detector 130. The system 100 may further include one or more beam splitters and/or filters 122, 126 that direct a portion of the light from the lens 120 toward additional light detectors 124, 128. For example, some of the particles in the fluid stream 109 may be induced by the light source 102 to fluoresce at a particular wavelength. One or more of the filters and/or light detectors may be configured to detect the fluorescent wavelength.

The peripheral light detectors 119 provide a means for identifying light signals having a significant component incident on the light deflectors 118, which information may be used to selectively identify or exclude data received by the light detectors 124, 128, 130. For example, in an exemplary system, the light resulting from interactions of particles 112 in the sensing region 111 that are not in a focal area of the sensing region 111 produces a larger component incident on the light deflectors 118 and therefore produces larger signals from the peripheral detectors 119. The larger signals from the peripheral detectors can therefore be used to identify corresponding signals in the parametric detectors 124, 128, and 130 that are not in the focal region, and such signals may be excluded from further analysis.

In the system 100, a beam splitter 115 is positioned, preferably at an angle of approximately forty-five degrees relative to the optical axis 99, and disposed between the lens 114 and the field stop 117. The beam splitter 115 allows most of the light from the lens 114 to pass through towards the aperture 116 and reflects an image of the field stop 117 through a lens 113 towards a suitably positioned imaging device 103, for example, a CCD video camera. To improve the reflected image, the field stop 117 preferably has a mirrored surface facing the beam splitter 115. Although a simple substantially transparent beam splitter 115 is used in a current embodiment, as used herein, "beam splitter" is defined to include other suitable optical elements, including, for example, a dichroic mirror/filter for which only a small band or range of frequency (some portion of that small band) is deflected towards the camera, this band being used for beam position information and allowing other bands to pass through substantially unaffected. The dichroic filter is advantageous because it is desirable to allow as much of the light information as possible to pass through the field stop aperture.

The imaging device 103 is in signal communication with a computing apparatus 121 and transmits the image data of the field stop 117 (through reflection from the beam splitter 113) to the computing apparatus 121. The image data is processed by the computing apparatus 121, for example, as described below; and corresponding control signals are sent from the computing apparatus 121 to an XY stage 123 comprising servomotors (indicated by arrows 129) that adjust the position of the XY stage 123. In the system 100, the beam from the light source 102 is directed towards the sensing region 111 through a light deflector 127 (for example, a prism) and a lens 125 that are mounted on the XY stage 123. The signals from the computing apparatus 121 command the servomotors 129 to position the XY stage 123 for up-down motion (in and out of the page) and side-to-side motion (up and down in FIG. 1).

Figure 2:
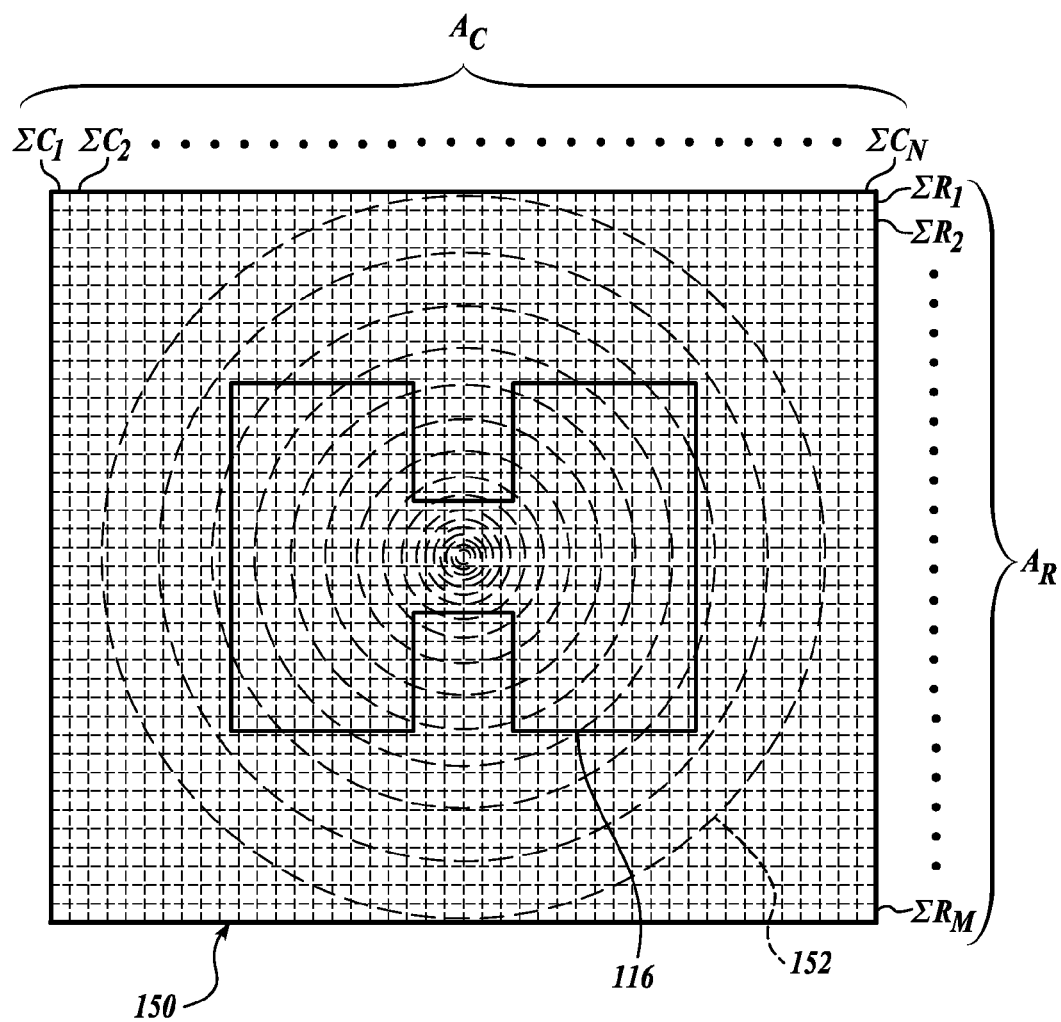
FIG. 2 illustrates an exemplary image taken by the imaging device of the cytometry system shown in FIG. 1.

FIG. 2 illustrates an idealized video image 150 from the imaging device 103, showing a reflected image of at least a portion of the field stop 117 with the H-shaped optical aperture 116. The image 150 is preferably a digital image comprising a two-dimensional array of pixels, each pixel having at least one corresponding intensity value that defines the image 150. The image may include a relatively bright (e.g., high intensity) central portion 152 that will in general be quite complicated in shape and pattern due to complexities in the interactions of the light beam and the geometry of the system 100. The bright portion 152, however, includes information regarding the alignment of the light beam from the laser(s) 102 with the sensing region 111 and the field stop 117.

In the present method, the digital image intensity values are combined (for example, summed) in two orthogonal directions (e.g., rows and columns). In FIG. 2, $\Sigma C_1, \Sigma C_2 \ldots \Sigma C_N$ indicates the column sums of pixel intensity and $\Sigma R_1$, $\Sigma R_1 \ldots \Sigma R_M$ indicates the row sums of pixel intensity. The column sums are stored in an array $A_C$, and the row sums are stored in an array $A_R$.

Figure 3A:
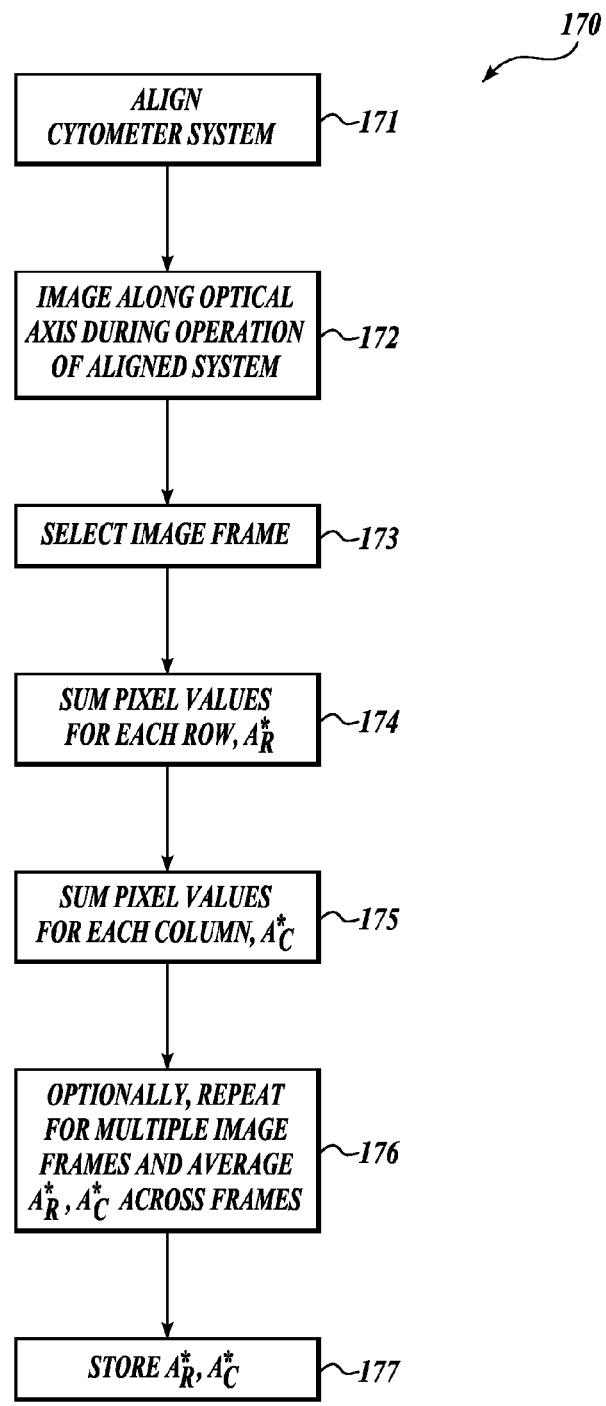
FIGS. 3A and 3B are flow charts outlining an embodiment of the method disclosed herein, wherein FIG. 3A discloses a method for generating row and column arrays for an aligned cytometry system, and FIG. 3B discloses a method for monitoring and controlling the system using the aligned cytometry arrays.
Figure 3B:
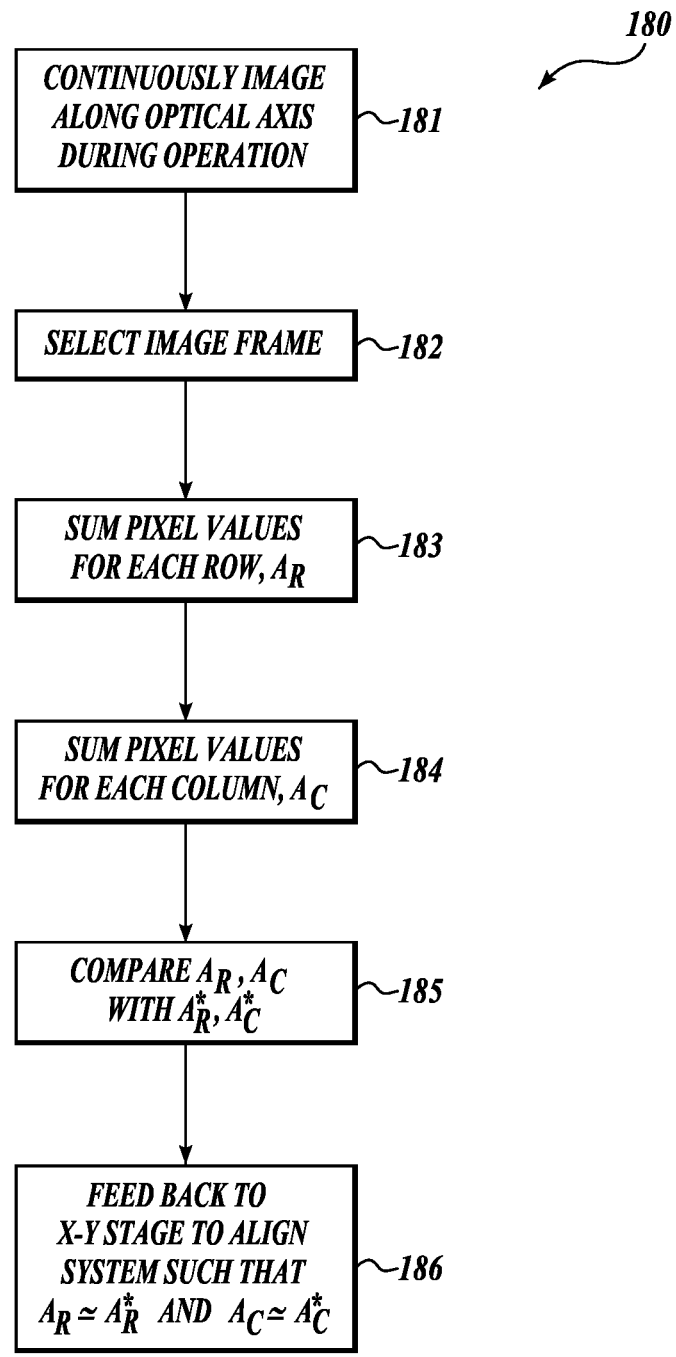

FIGS. 3A and 3B present flow charts describing a method in accordance with the present invention. In FIG. 3A, a method 170 for generating an array of column and row sums for an aligned system 100 is shown. The cytometer system is first tuned or aligned 171 with the system 100 operating. The alignment may be performed manually or auto-aligned. For example, if the system has been calibrated, the system can first be auto-aligned to the calibration. An image from the beam splitter 115 is obtained for the aligned system 172. If a motion video imaging system is used, an image frame is selected 173. Optionally, two or more image frames may be selected and the average intensity values at each pixel may be used to reduce noise.

The pixel intensity values for each row are then calculated to generate a row array for the aligned system, $A_R^*$ 174. The pixel intensity values for each column of the image are similarly calculated to generate a column array, $A_C^*$ 175, for the aligned system. Optionally, this calculation may be done for two or more image arrays, and the averaged values across frames used for each row and column 176. The row and column arrays $A_R^*$, $A_C^*$ are then stored 177.

The row and column arrays for the aligned system 100 can then be used to maintain the system 100 in alignment, adjusting for factors such as thermal changes, laser pointing instability, etc., during regular operation of the cytometer 180. The imaging device 103 monitors the beam splitter 115, preferably continuously, during operation 181. Images from the device 103 are periodically selected 182, and the row and column pixel intensity values are calculated 183, 184. As noted above, more than one image frame may be averaged or otherwise combined, to reduce noise.

The array of row sums $A_R$ and column sums $A_C$ may then be compared with the corresponding stored arrays $A_R^*$, $A_C^*$ for the aligned system and used to feed back to the XY stage 123 to selectively control the alignment of the light beam with the sensing region 186.

In a current embodiment, a proportional-integral-derivative (PID) control for the XY stage 123 was selected for the control loop. PID control is well-known to persons of skill in the art. For example, in a first direction (e.g., for the X-direction servomotor) $A_R$ may be subtracted from $A_R^*$ to generate the proportional term in the first direction, and similarly $A_C$ may be subtracted from $A_C^*$ to generate the proportion term in the second direction. The contribution from the integral term is proportional to both the magnitude of the error and the duration of the error. Summing the instantaneous error over time gives the accumulated offset that should have been corrected. The accumulated error is then multiplied by the integral gain and added to the controller output. The rate of change of the process error may be calculated by determining the slope of the error over time and multiplying this rate of change by the derivative gain. The derivative term slows the rate of change of the controller output. The proportional, integral, and derivative terms are summed to calculate the PID controller.

Figure 4:
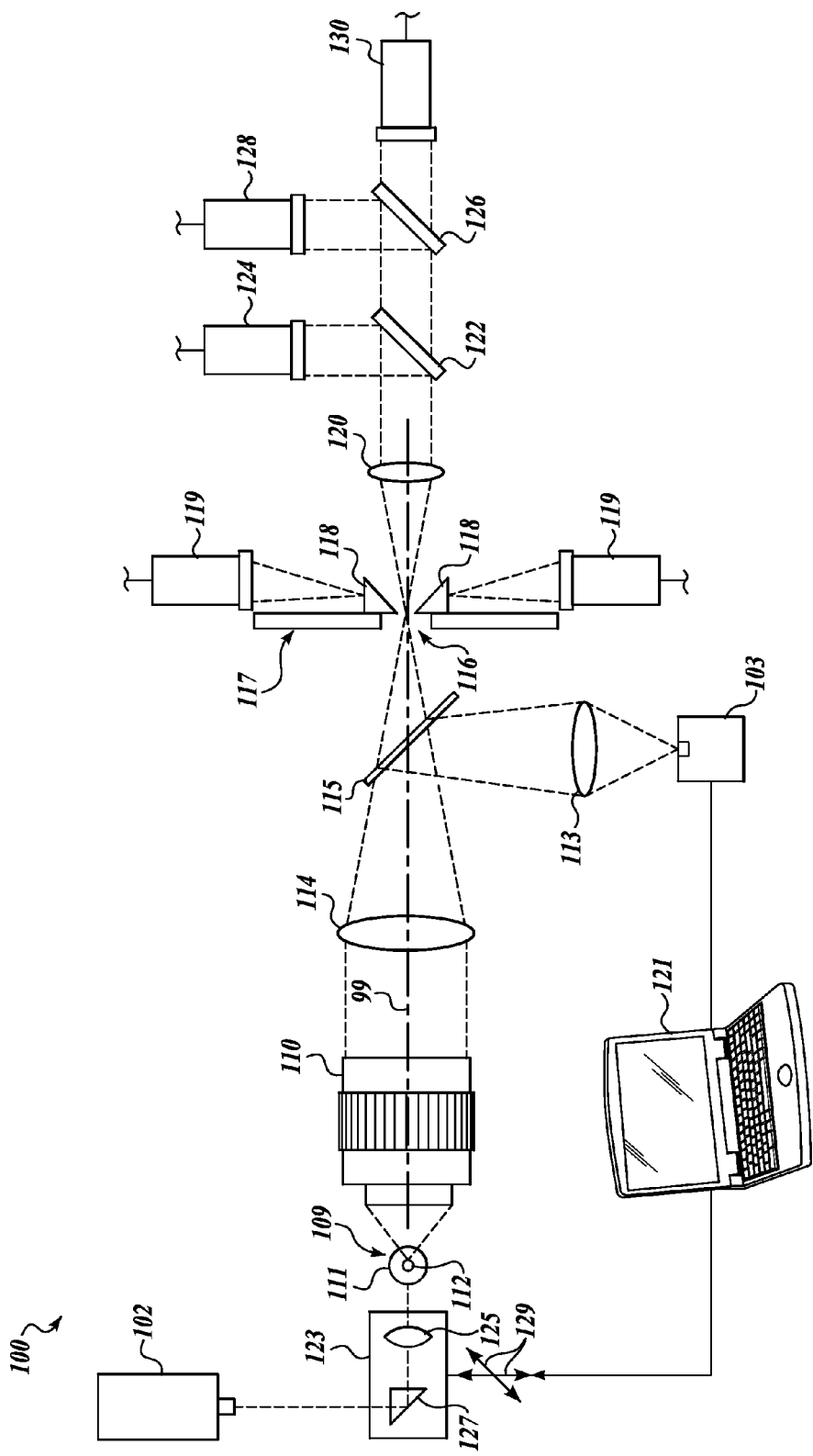
FIG. 4 shows schematically a second embodiment of a cytometry system in accordance with the present invention.

FIG. 4 shows a second embodiment of a cytometer system 200 in accordance with the present invention. The second embodiment is very similar to the system 100 described above, and the various aspects that are in common will not be described here, for brevity.

As will be apparent by comparing FIG. 1 with FIG. 4, in the system 200 the beam splitter 115 is oriented to reflect an image 'upstream' of the field stop 117 rather than of the field stop 117 itself. The beam splitter, therefore, images (to the left in FIG. 4) through the lens 114 and objective 110 towards the sensing region 111. The system 200 is otherwise identical to the prior system, and the method for continuously controlling the alignment of the system 200 may be performed in accordance with FIGS. 3A and 3B, as described in more detail above. It will be appreciated, therefore, that the method does not rely on imaging any portion of the field stop 117, but rather may be readily implemented imaging towards the fluid stream sensing region 111.

While illustrative embodiments have been illustrated and described, it will be appreciated that various changes can be made therein without departing from the spirit and scope of the invention. For example, although the XY stage 123 is shown to support only certain optical elements (lens 125 and prism 127), the laser may alternatively be supported directly on the XY stage 123 and/or additional optical components my be incorporated. It will also be appreciated by persons of skill in the art that control loop feedback mechanisms other than PID control are known and may alternatively be used.

The embodiments of the invention in which an exclusive property or privilege is claimed are defined as follows:

1. A flow cytometry system operable to examine a fluid stream having particles suspended therein, the cytometry system comprising:
   a light source focused on a sensing region in the fluid stream;
   an objective positioned to receive light from the sensing region;
   a lens positioned to receive light from the objective, wherein the lens and objective define an optical axis;
   a field stop having an aperture;
   a beam splitter that is positioned between the lens and the field stop that intersects the optical axis at an angle;
   an imaging device positioned to generate images from light received from the beam splitter, the beam splitter and imaging device being oriented such that the generated images are along the optical axis;
   an XY stage defining a support surface that is precisely controllable in at least two orthogonal directions, wherein the XY stage supports an optical element that determines the alignment of the light source with respect to the sensing region;
   a computing device that receives the images generated by the imaging device and calculates from the images at least one parameter that characterizes the alignment of the light source with the sensing region, wherein the at least one calculated parameter is used to generate control signals that are transmitted to the XY stage such that a desired alignment of the light source with the sensing region is maintained.

2. The system of claim 1, wherein the light source comprises at least one laser.

3. The system of claim 1, wherein the beam splitter comprises a dichroic filter.

4. The system of claim 2, wherein the generated images comprise digital images defined by a two-dimensional array of pixels, each pixel having an intensity, and wherein the at least one parameter calculated by the computing device comprises a first array of values characterizing the pixel intensities along each row of pixels and a second array of values characterizing the pixel intensities along each column of pixels.

5. The system of claim 2, wherein the at least one calculated parameter that characterizes the alignment of the light source comprises a first parameter that characterizes the alignment with respect to a first direction and a second parameter that characterizes the alignment with respect to a second direction orthogonal to the first direction.

6. The system of claim 5, wherein the generated images comprise digital images defined by a two-dimensional array of pixels, each pixel having an intensity, and further wherein the first parameter comprises a first array of the row sum of the image pixel intensities and the second parameter comprises a second array of the column sum of the image pixel intensities.

7. The system of claim 4, wherein the generated control signals to the XY stage are calculated using a control algorithm.

8. The system of claim 7, wherein the control algorithm is a proportional-integral-derivative control algorithm.

9. The system of claim 4, wherein the XY stage includes a plurality of stepper motors that control the position of the XY stage in response to the transmitted control signals.

10. The system of claim 4, wherein the system further comprises a plurality of light detectors that receive light from the objective that passes through the field stop aperture during operation.

11. The system of claim 4, wherein the field stop aperture is H-shaped, having relatively large end portions and a relatively small center portion, the system further comprising first and second light deflectors disposed over the relatively large end portions, and associated first and second light detectors that receive light deflected by the first and second light deflectors, respectively.

12. The system of claim 11, wherein the light deflectors comprise prisms.

13. A method for performing flow cytometry of a fluid stream having a plurality of particles suspended therein with a cytometer, the method comprising:
  focusing a light source on a sensing region of the fluid stream;
  using an optical system, receiving light from the sensing region of the fluid stream and focusing the received light along an optical axis that intersects a field stop having an aperture;
  providing a beam splitter between the optical system and the field stop that is positioned to intersect the optical axis at an angle;
  with the cytometer operating, aligning the cytometer;
  imaging the beam splitter with an imaging device wherein the beam splitter and camera are aligned to produce an image along the optical axis;
  providing an XY stage defining a support surface that is controllable in at least two orthogonal directions, wherein the XY stage supports an optical element that determines the alignment of the light source with respect to the sensing region; and
  calculating from the image along the optical axis a parameter that characterizes the alignment of the light source with the sensing region for the aligned system;
  during continuous operation of the cytometer, imaging the beam splitter with the imaging device to generate a plurality of images along the optical axis;
  calculating from the plurality of images the parameter that characterizes the alignment of the light source with the imaging region for the continuously operated cytometer;
  comparing the parameter calculated for the aligned system with the parameter calculated for the continuously operated cytometer to determine control signals for the XY stage; and
  sending the control signals to the XY stage such that the optical element that determines the alignment of the light source is maintained in an aligned position.

14. The method of claim 13, wherein the light source comprises a laser.

15. The method of claim 13, wherein the beam splitter comprises a dichroic filter.

16. The method of claim 13, wherein the images along the optical axis comprise two dimensional arrays of pixels, each pixel having an intensity value, and wherein the parameter characterizing the alignment of the light source comprises arrays of a row sum and a column sum of the pixel intensity values.

17. The method of claim 13, wherein the step of calculating from the image along the optical axis a parameter that characterizes the alignment of the light source with the sensing region comprises calculating a first parameter that characterizes the alignment with respect to a first direction and a second parameter that characterizes the alignment with respect to a second direction orthogonal to the first direction.

18. The method of claim 13, wherein the step of comparing the parameter calculated for the aligned system with the parameter calculated for the continuously operated cytometer to determine control signals for the XY stage comprises implementing a proportional-integral-derivative control algorithm.

19. The method of claim 13, wherein the XY stage includes a plurality of stepper motors that control the position of the XY stage in response to the transmitted control signals.

20. The method of claim 13, further comprising providing a plurality of light detectors that receive light from the objective that passes through the field stop aperture during operation.

21. The method of claim 20, wherein the field stop aperture is H-shaped, having relatively large end portions and a relatively small center portion.

22. The apparatus of claim 1, wherein the field stop comprises a mirrored surface that faces the beam splitter.

23. The method of claim 13, wherein the field stop comprises a mirrored surface that faces the beam splitter.

* * * * *